United States Patent
Gerard et al.

(10) Patent No.: US 7,317,524 B2
(45) Date of Patent: Jan. 8, 2008

(54) METHOD AND DEVICE FOR DETECTING SURFACE DEFECTS ON THE NECK RING OF A TRANSPARENT OR TRANSLUCENT CONTAINER OF REVOLUTION

(75) Inventors: Marc Gerard, Givors (FR); Guillaume Bathelet, Lyons (FR)

(73) Assignee: Tiama, Montagny (FR)

( * ) Notice: Subject to any disclaimer, the term of this patent is extended or adjusted under 35 U.S.C. 154(b) by 60 days.

(21) Appl. No.: 10/532,608

(22) PCT Filed: Oct. 24, 2003

(86) PCT No.: PCT/FR03/03166

§ 371 (c)(1),
(2), (4) Date: Oct. 28, 2005

(87) PCT Pub. No.: WO2004/040278

PCT Pub. Date: May 13, 2004

(65) Prior Publication Data

US 2006/0119842 A1    Jun. 8, 2006

(30) Foreign Application Priority Data

Oct. 25, 2002  (FR) ................... 02 13357

(51) Int. Cl.
*G01J 3/00* (2006.01)
*G01B 11/24* (2006.01)
*G01B 11/28* (2006.01)

(52) U.S. Cl. .................. 356/300; 259/601; 259/629

(58) Field of Classification Search ............... 209/526; 250/223 B; 356/239.4
See application file for complete search history.

(56) References Cited

U.S. PATENT DOCUMENTS

| | | | | | |
|---|---|---|---|---|---|
| 3,349,906 | A | * | 10/1967 | Calhoun | 209/526 |
| 3,557,950 | A | * | 1/1971 | Powers | 209/526 |
| 3,631,255 | A | * | 12/1971 | Gender et al. | 250/223 B |
| 3,829,690 | A | * | 8/1974 | Snyder | 250/302 |
| 3,974,378 | A | * | 8/1976 | Brugger | 250/223 B |
| 4,021,122 | A | * | 5/1977 | Krenmayr | 356/239.4 |
| 4,026,414 | A | * | 5/1977 | Ellinger | 209/524 |

(Continued)

FOREIGN PATENT DOCUMENTS

EP   0061021   2/1982

(Continued)

*Primary Examiner*—Gregory J. Toatley, Jr.
*Assistant Examiner*—Jarreas Underwood
(74) *Attorney, Agent, or Firm*—Clark & Brody

(57) ABSTRACT

A device for detecting surface defects (2) on the neck ring (3) of a container comprises:
a light source (5) illuminating, by means of an incident light beam, a section of the surface of the neck ring of the container, along a determined incident direction ($D_i$),
at least one linear sensor (10) measuring light beams, arranged to receive the light beam reflected by the surface defect, the angle ($\alpha$) between the incident ($D_i$) and reflection ($D_r$) directions lying between 15 and 45°, preferably in the order of 30°, one of the directions being parallel to the axis of revolution of the container,
means (15) for ensuring the rotation of the container about the axis of revolution through at least one rotation,
and a unit (16) for analysing and processing light beams received by the linear sensor, to identify the presence of a surface defect.

14 Claims, 3 Drawing Sheets

U.S. PATENT DOCUMENTS

| | | | |
|---|---|---|---|
| 4,424,441 A | | 1/1984 | Bieringer et al. |
| 4,664,525 A | * | 5/1987 | Tagaya ........................ 356/428 |
| 4,914,289 A | * | 4/1990 | Nguyen et al. ......... 250/223 B |
| 4,929,828 A | * | 5/1990 | Claypool ................ 250/223 B |
| 5,592,286 A | | 1/1997 | Fedor |
| 6,025,909 A | * | 2/2000 | Juvinall et al. .......... 356/239.4 |
| 2001/0048524 A1 | * | 12/2001 | Sones ...................... 356/239.4 |

FOREIGN PATENT DOCUMENTS

| | | |
|---|---|---|
| EP | 0371546 | 11/1989 |
| EP | 0497477 A2 | 1/1992 |
| JP | 10-62359 | 3/1998 |

\* cited by examiner

METHOD AND DEVICE FOR DETECTING SURFACE DEFECTS ON THE NECK RING OF A TRANSPARENT OR TRANSLUCENT CONTAINER OF REVOLUTION

FIELD OF THE INVENTION

The present invention concerns the technical area of inspecting objects, hollow items or, generally any transparent or translucent containers such as glass bottles, flasks or jars.

BACKGROUND OF THE INVENTION

The subject of the invention more precisely concerns the inspection of such containers to detect the presence of surface defects on the neck ring of said containers, such as a material defect, called line defect corresponding to excess or shortage of material (line over finish), defects called seeds or blisters, or defects corresponding to a chipped ring.

The state of the art proposes various devices for inspecting the quality of container neck rings so as to eliminate those carrying defects which may detract from their appearance or, more seriously, constitute a true hazard for users. For example, a detection device is known through documents EP 0 497 477 or JP 10 062 359, comprising a light source able to provide an incident beam concentrated on the upper surface of the neck ring. A camera is positioned so as to receive the reflected light beams which are transmitted to a processing unit, adapted to re-constitute an image of the ring surface after rotating the object on a lathe. The processing unit analyses variations of the image in time and space to detect the presence of any defects. Said technical solution does not give satisfaction in practice, insofar as the images suffer from extensive stray light due to the different light reflections on the surface of the container. Surface irregularities of the neck ring generate extensive noise and mask minor defects such as line defects.

BRIEF SUMMARY OF THE INVENTION

The purpose of the invention is to overcome the aforementioned drawbacks by putting forward a reliable detection solution to detect, on the neck ring of a transparent or translucent container having an axis of revolution, any surface defects that are generally difficult to detect such as line defects.

To attain this objective, the subject of the invention sets out to propose a method to detect surface defects on the neck ring of a transparent or translucent container having an axis of revolution, which comprises the following steps:

illuminating a section of the neck ring surface of the container with an incident light beam, along a determined incident direction, arranging a linear measuring sensor along a determined direction of reflection, to collect the light beam reflected by the surface defect on the neck ring, the angle between the incident and reflection directions lying between 15 and 45°, preferably in the order of 30°, one of the directions being parallel to the axis of revolution of the container, ensuring rotation of the container about the axis of revolution through at least one revolution, and processing the light beams received by the linear sensor so as to create and analyse an image to identify the presence of any surface defect corresponding to a bright area.

According to a preferred characteristic of embodiment, the method consists of using an incident light beam to illuminate a radial section of the neck ring surface of the container.

According to this preferred variant of embodiment, one of the directions of reflection or incidence is parallel to the axis of revolution of the container, whilst the other direction extends along a plane perpendicular to the radial plane of the container and parallel to the axis of revolution.

According to one advantageous characteristic of embodiment, the method consists of analysing the image by conducting an analysis of the form characteristics of the bright areas, so as to identify the presence of a surface defect.

According to another advantageous characteristic of embodiment, the method consists of using an incident light beam to illuminate a radial section of the neck ring surface of a container along a determined incident direction, parallel to the axis of revolution of the container, and of arranging a linear measuring sensor parallel to the radial plane and oriented along a direction extending in a plane perpendicular to the radial plane and parallel to the axis of revolution.

According to this advantageous characteristic of embodiment, the method consists of arranging a second linear measuring sensor symmetrical to the first linear measuring sensor with respect to the radial plane.

A further subject of the invention is to propose a device for detecting surface defects on the neck ring of a transparent or translucent container having an axis of revolution, the device comprising:

a light source adapted to illuminate, with an incident light beam, a section of the neck ring surface of the container, along a determined incident direction, at least one linear sensor for measuring the light beam, arranged to receive the light beam reflected by the surface defect of the neck ring, the angle between the incident and reflection directions lying between 15 and 45°, preferably in the order of 30°, one of the directions being parallel to the axis of revolution of the container, means ensuring rotation of the container about the axis of revolution through at least one revolution, and an analysis and processing unit for the light beams received by the linear sensor and adapted to create an image and analysis the image, so as to identify the presence of a surface defect corresponding to a bright area.

According to a preferred characteristic of embodiment, the light source illuminates a radial section of the neck ring surface of the container with an incident light beam.

Advantageously, the light source and the linear measuring sensor are positioned so that either one of the reflection or incident directions is parallel to the axis of revolution of the container, whilst the other direction extends along a plane perpendicular to the radial plane of the container and parallel to the axis of revolution.

According to a preferred characteristic of embodiment, the analysis and processing unit comprises means for analysing the form characteristics of the bright areas so as to identify the presence of a surface defect.

According to a preferred variant of embodiment, the light source illuminates a radial section of the ring surface of the container with an incident light beam, the linear measuring sensor being positioned parallel to the radial plane and being oriented along a direction extending in a plane perpendicular to the radial plane and parallel to the axis of revolution.

Advantageously, the device of the invention comprises a second linear measuring sensor, positioned symmetrically to the first linear measuring sensor with respect to the radial plane.

BRIEF DESCRIPTION OF THE DRAWINGS

Various other characteristics will become apparent from the description given below with reference to the appended drawings which show non-restrictive examples of embodiments of the subject of the invention.

DETAILED DESCRIPTION OF THE INVENTION

Figure 1:
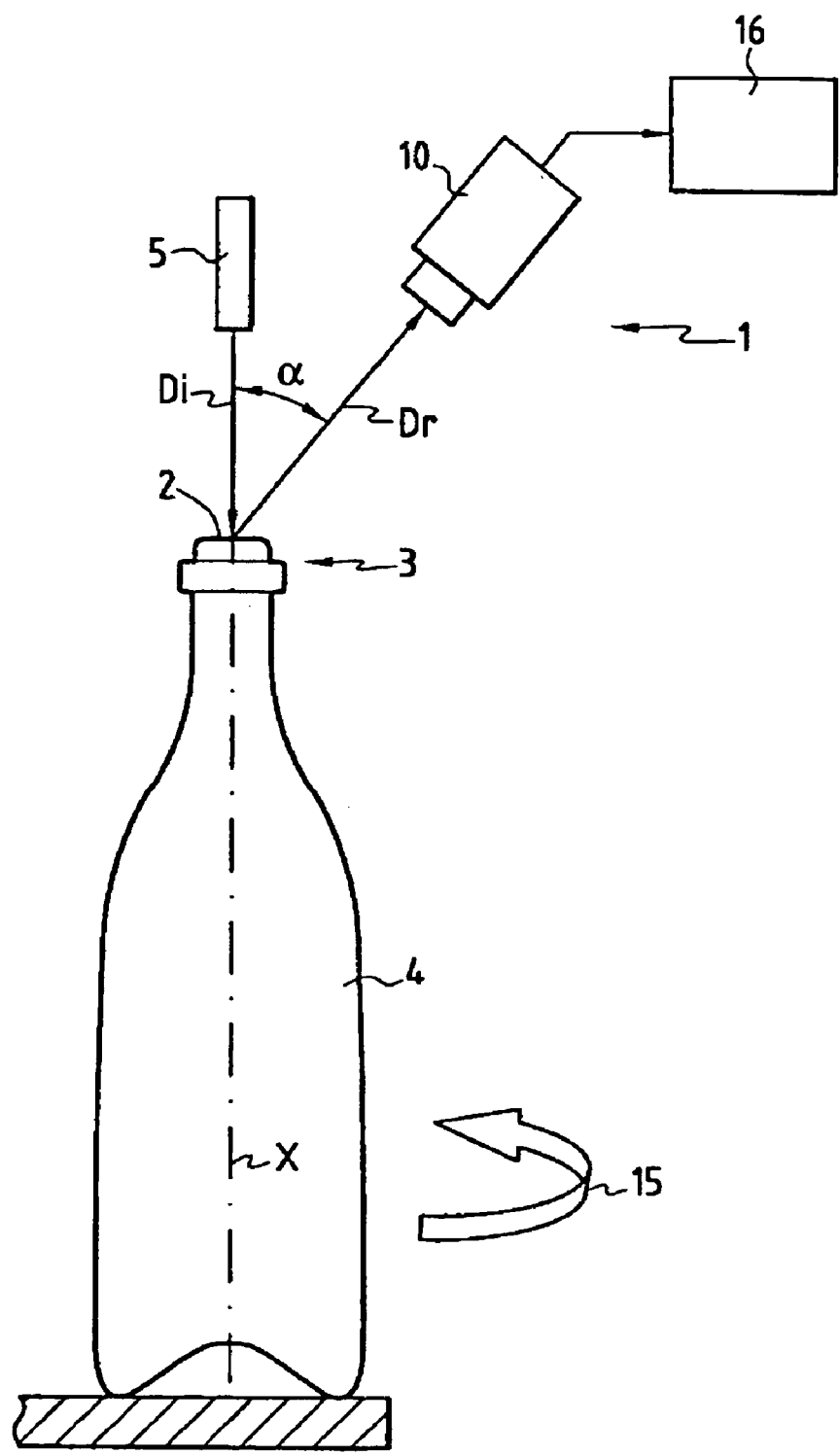
FIG. 1 is a schematic elevation view illustrating the implementation of a detection device according to the invention.
Figure 2A:
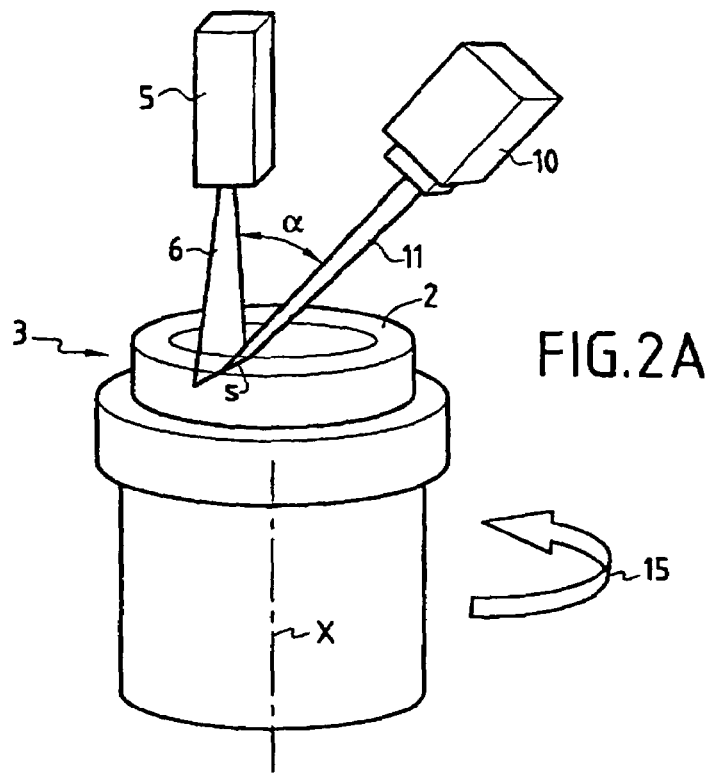
FIGS. 2a and 2b are perspective views illustrating the operating principle of the detection device of the invention.
Figure 2B:
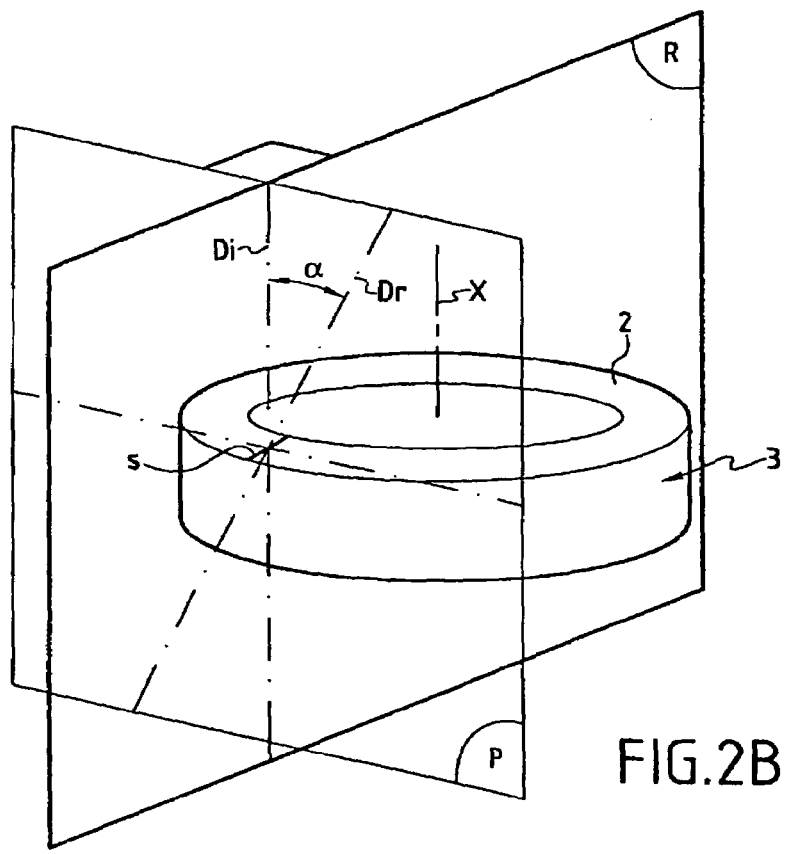
Figure 3:
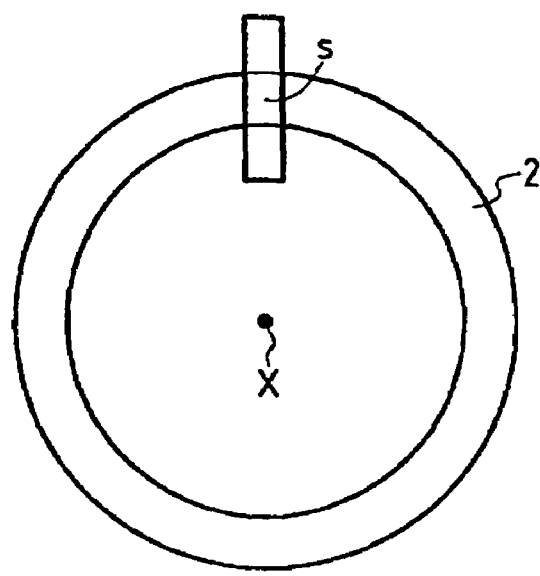
FIG. 3 is a schematic, showing a cross-section view of a container, illustrating the projection of light beams by the detection device of the invention.

As emerges more precisely from FIGS. 1 to 3, the subject of the invention concerns a method and a device 1, adapted to detect defects on the surface 2 of a neck ring 3 of a transparent or translucent container 4 having an axis of revolution or symmetry X. Said device 1 comprises a light source 5 adapted to illuminate, via an incident light beam 6, a section s of surface 2 of the container neck ring along a determined incident direction $D_i$.

According to a preferred characteristic of embodiment, the light source 5 via an incident light beam 6, illuminates a radial section s of surface 2 of the container neck ring, as can be seen precisely in FIG. 3. The radial section s of surface 2 of the neck ring therefore relates to the thickness of a wall of container 4 at the surface 2 of the neck ring and in a plane passing through the axis of revolution X. In the example of embodiment illustrated in the drawings, the light source 5 is positioned so as to illunmiate, via its incident light beam 6, a radial section s of surface 2 of the neck ring 3 of container 4, along a determined incident direction $D_i$ parallel to the axis of revolution X of the container (FIG. 2b).

Device 1 of the invention also comprises at least one linear sensor 10 for measuring light beams, arranged to receive the light beams 11 reflected by defects on the surface 2 of neck ring 3 of the container. The linear measuring sensor 10, such as a camera, is positioned to collect the light beams 11 reflected by section s of surface 2 of the neck ring. In this respect, the line of photosensitive cells of camera 10 is oreinted along a direction parallel to section s of surface 2 illuminated by the incident beam 6. In the preferred example of embodiment, for which the light source 5 illuminates a radial section s of the neck ring of the container, the linear measuring sensor 10 is positioned parallel to the radial plane R.

Also, the sighting axis of the camera 10, schematised by the reflected light beam 11, therefore extends along a direction of reflection $D_r$ which, with the incident direction $D_i$, forms an angle α of between 15 and 45° preferably in the order of 30°. In the preferred example of embodiment illustrated in the drawings and in which the light source 5 illuminates a radial section s of the neck ring, camera 10 is oriented along a direction of reflection $D_r$ in a plane P perpendicular to the radial plane R and parallel to the axis of revolution X (FIG. 2b). Evidently, this plane P, along which the sighting axis of camera 10 extends, cuts the radial section s of the ring illuminated by the incident light beam 6, so that the line of photosensitive cells is able to scan section s of surface 2 of the neck ring, over a given elementary width.

In the illustrated example, it is to be noted that the incident direction $D_i$ of the light beam is parallel to the axis of revolution X of the container. Evidently, the position between the light source 5 and the linear measuring sensor 10 may be interchanged. According to this variant of embodiment, the direction of reflection $D_r$, in which camera 10 is positioned, is parallel to the axis of revolution X of the container, while the incident direction $D_i$ of the incident light beam 6 is inclined so that, with the direction of reflection $D_r$, it forms angle α previously defined.

The relative positioning of light source 5 and the linear measuring sensor 10, makes it possible to recover only the light reflected by the defects on surface 2 of the neck ring 3. The linear measuring sensor 10 is positioned so as not to receive the light reflected by the ring surface not having any defects. In the example of embodiment illustrated in the drawings, the incident light 6, parallel to the axis of revolution X of the container, is transmitted or reflected along the same axis when ring surface 2 does not have any defects. Therefore, only part of the light reflected by the defects of surface 2 at angle α is detected by the camera 10. In this manner, the surface defects are not masked by the direct reflection of surface 2. Said method of detection provides reliable, efficient detection even for minor surface defects.

The detection device 1 of the invention also comprises means 15 ensuring the rotation of the container 4 about its axis of revolution X through at least one complete rotation so that the camera scans the entirety of surface 2 of the neck ring 3 of container 4. Rotation of the container 4 about its axis of revolution X enables the camera to successively visualize each of section s of elementary width which together form the surface 2 of neck ring 3.

Detection device 1 of the invention also comprises an analysis and processing unit 16 connected to the linear measuring sensor 10. This unit 16 for analysing and processing the light beams received by the linear sensor 10 is adapted to create an image and analyse the image so as to identify, within the image, the presence of any surface defect corresponding to a bright area. As explained above, the linear sensor 10 is positioned so as to remover the light flow reflected by the defect.

Figure 4:
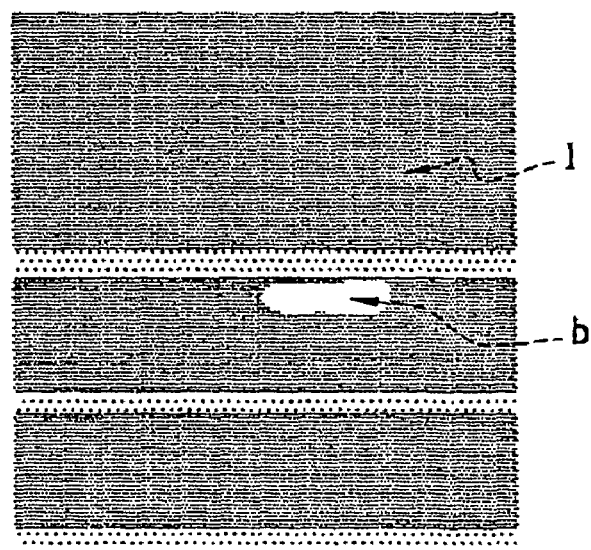
FIG. 4 is a picture taken by a detection device of the invention.

The input of the analysis and processing unit 16, as is usual, comprises an acquisition circuit having an input connection to the camera which delivers electronic signals representing the light intensity received by each of the camera's photosensitive cells. The acquisition circuit ensures conversion of the analogue signal into a digital signal coded in a certain number of bits in accordance with a determined scale of greys. This raw image is memorized and filtered to attenuate image contrasts. The filtered image is subtracted from the raw image to remove interference so as to obtain a final image I, such as illustrated in FIG. 4. As explained above, the defects appear in the form of a bright area b, since it corresponds to the light reflected by the defects. Unit 16 comprises image analysis means based on analysis of the form characteristics of bright areas b, to identify the presence of a surface defect. These analysis means are used to calculate characteristics such as the position in space, surface, perimeter, centre of gravity or level of grey of the bright areas. Said characteristics are compared with threshold values to determine whether or not the detected bright area b corresponds to a defect.

According to a further characteristic of the invention, it is to be noted that the detection device 1 may comprise a second linear measuring sensor, positioned symmetrically to the first linear measuring sensor 10 with respect to radial plane R. In this variant, the second linear measuring sensor is positioned parallel to the radial plane R, being oriented in a direction extending along the perpendicular plane P with an angle of incline α of opposite direction with respect to direction $D_i$.

The invention is not limited to the examples shown and described since various modifications may be made thereto without departing from the scope of the invention.

The invention claimed is:

1. Method for detecting surface defects (2), on a neck ring (3), of a transparent or translucent container (4) having an axis of revolution (X), characterized in that it comprises the following steps:
    illuminating, by means of an incident light beam (6), a section (s) of the surface (2) of the neck ring (3) of the container (4), along a determined incident direction ($D_i$),
    arranging a linear measuring sensor (10), along a determined direction of reflection ($D_r$), to collect the light beam reflected by the surface defect on the neck ring, the angle (α) between the incident direction ($D_i$) and reflection direction ($D_r$) lying between 15 and 45°, preferably in the order of 30°, one of these directions being parallel to the axis of revolution (X) of the container while the other direction extends along a plane (P) perpendicular to the radial plane (R),
    ensuring rotation of the container (4) about the axis of revolution (X) through at least one rotation,
    and processing the light beam received by the linear sensor (10), so as to create an image (I) and analyse the image to identify the presence of a surface defect corresponding to a bright area (b),
    wherein one of the reflection ($D_r$) or incident ($D_i$) directions is parallel to the axis of revolution (X) of the container while the other direction extends along a plane (P) perpendicular to the radial plane (R) of the container and parallel to the axis of revolution (X).

2. Method as in claim 1, characterized in that it consists of illuminating, by means of an incident light beam (6), a radial section (s) of surface (2) of the container's neck ring.

3. Method as in claim 1, characterized in that it consists of analysing the image (I) by conducting an analysis of the form characteristics of the bright areas (b) in order to identify the presence of a surface defect.

4. Method as in claim 1, characterized in that it consists of illuminating, by means of an incident light beam (6), a radial section (s) of the surface (2) of the container's neck ring (4) along a determined incident direction parallel to the axis of revolution (X) of the container, and of arranging a linear measuring sensor (10) parallel to the radial plane (R) and oriented in a direction extending along a plane (P) perpendicular to the radial plane and parallel to the axis of revolution.

5. Method as in claim 4, characterized in that it consists of arranging a second linear sensor symmetrically to the first linear measuring sensor (10) with respect to the radial plane (R).

6. Device for detecting surface defects (2) on the neck ring (3) of a transparent or translucent container (4) having an axis of revolution (X), characterized in that it comprises:
    a light source (5) adapted to illuminate by means of an incident light beam (6), a section (s) of the neck ring surface of the container, along a determined incident direction ($D_i$),
    at least one linear measuring sensor (10) to measure light beams arranged to collect the light beam reflected by the surface defect on the neck ring, the angle (α) between the incident ($D_i$) and reflection ($D_r$) directions lying between 15 and 45°, preferably in the order of 30°, one of the directions being parallel to the axis of revolution (X) of the container while the other direction extends along a plane (P) perpendicular to the radial plane (R),
    means (15) for ensuring rotation of the container about the axis of revolution through at least one rotation,
    and a unit (16) for analysing and processing the light beams received by the linear sensor, adapted to create an image (I) and to analyse the image so as to identify the presence of a surface defect corresponding to a bright area (b),
    wherein the light source (5) and the linear measuring sensor (10) are positioned so that either one of the reflection ($D_r$) or incident ($D_i$) directions is parallel to the axis of revolution (X) of the container, while the other direction extends along a plane (P) perpendicular to the radial plane (R) of the container and parallel to the axis of revolution (X).

7. Device as in claim 6, characterized in that the light source (5), by means of an incident light beam (6), illuminates a radial section (s) of the surface (2) of the container's neck ring.

8. Device as in claim 6, characterized in that the analysis and processing unit (16) comprises means for analysing the form characteristics of the bright areas (b) in order to identify the presence of a surface defect.

9. Device as in claim 6, characterized in that the light source (5) by means of an incident light beam (6), illuminates a radial section (s) of the surface (2) of the neck ring of the container along a determined incident direction ($D_i$) parallel to the axis of revolution (X) of the container, and in that the linear measuring sensor (10) is positioned parallel to the radial plane (R), being oriented in a direction extending along a plane (P) perpendicular to the radial plane and parallel to the axis of revolution (X).

10. Device as in claim 9, characterized in that it comprises a second linear measuring sensor (10) positioned symmetrically to the first linear measuring sensor with respect to the radial plane (R).

11. Method for detecting surface defects (2), on a neck ring (3), of a transparent or translucent container (4) having an axis of revolution (X), characterized in that it comprises the following steps:
    illuminating, by means of an incident light beam (6), a section (s) of the surface (2) of the neck ring (3) of the container (4), along a determined incident direction ($D_i$),
    arranging a linear measuring sensor (10), along a determined direction of reflection ($D_r$), to collect the light beam reflected by the surface defect on the neck ring, the angle (α) between the incident direction ($D_i$) and reflection direction ($D_r$) lying between 15 and 45°, preferably in the order of 30°, one of these directions being parallel to the axis of revolution (X) of the container,
    ensuring rotation of the container (4) about the axis of revolution (X) through at least one rotation, and processing the light beam received by the linear sensor (10), so as to create an image (I) and analyse the image to identify the presence of a surface defect corresponding to a bright area (b), wherein the light source, by means of an incident light beam (6), illuminates a radial section (s) of the surface (2) of the container's neck ring (4) along a determined incident direction parallel to the axis of revolution (X) of the container, and of arranging a linear measuring sensor (10) parallel to the radial plane (R) and oriented in a direction extending along a plane (P) perpendicular to the radial plane and parallel to the axis of revolution.

12. Method as in claim 11, characterized in that it consists of arranging a second linear sensor symmetrically to the first linear measuring sensor (10) with respect to the radial plane (R).

13. Device for detecting surface defects (2) on the neck ring (3) of a transparent or translucent container (4) having an axis of revolution (X), characterized in that it comprises:

- a light source (5) adapted to illuminate by means of an incident light beam (6), a section (s) of the neck ring surface of the container, along a determined incident direction ($D_i$),
- at least one linear measuring sensor (10) to measure light beams arranged to collect the light beam reflected by the surface defect on the neck ring, the angle ($\alpha$) between the incident ($D_i$) and reflection ($D_r$) directions lying between 15 and 45°, preferably in the order of 30°, one of the directions being parallel to the axis of revolution (X) of the container,
- means (15) for ensuring rotation of the container about the axis of revolution through at least one rotation,
- and a unit (16) for analysing and processing the light beams received by the linear sensor, adapted to create an image (I) and to analyse the image so as to identify the presence of a surface defect corresponding to a bright area (b), wherein the light source (5) by means of an incident light beam (6), illuminates a radial section (s) of the surface (2) of the neck ring of the container along a determined incident direction ($D_i$) parallel to the axis of revolution (X) of the container, and in that the linear measuring sensor (10) is positioned parallel to the radial plane (R), being oriented in a direction extending along a plane (P) perpendicular to the radial plane and parallel to the axis of revolution (X).

14. Device as in claim 13, characterized in that it comprises a second linear measuring sensor (10) positioned symmetrically to the first linear measuring sensor with respect to the radial plane (R).

* * * * *